United States Patent [19]

Iida et al.

[11] 4,425,273

[45] Jan. 10, 1984

[54] PROCESS FOR PRODUCTION OF CHENODEOXYCHOLIC ACID

[76] Inventors: Takeshi Iida, 5-120, Aza Arai, Asaka-machi, Kouriyama-shi Fukushima-ken, Japan; Frederic C. Chang, Mt. San Antonio Gardens, Apt. A-22, 900 E. Harrison Ave., Pomona, Calif. 91767

[21] Appl. No.: 389,624

[22] Filed: Jun. 18, 1982

[30] Foreign Application Priority Data

Dec. 2, 1981 [JP] Japan ............................. 56-192823

[51] Int. Cl.³ .............................................. C07J 9/00
[52] U.S. Cl. ............................. 262/397.1; 260/239.5
[58] Field of Search ..................................... 260/397.1

[56] References Cited

U.S. PATENT DOCUMENTS 4,186,143  1/1980  Ziegler et al. ..................... 260/397.1

OTHER PUBLICATIONS

Chem. Abstracts (95), 1981, Par. 18753(a) an Abstract of Czech. Pat. to Halaskova, No. 186,067, filed Nov. 15, 1980.

*Primary Examiner*—Elbert L. Roberts
*Attorney, Agent, or Firm*—Sherman & Shalloway

[57] ABSTRACT

A process for producing chenodeoxycholic acid of the following formula

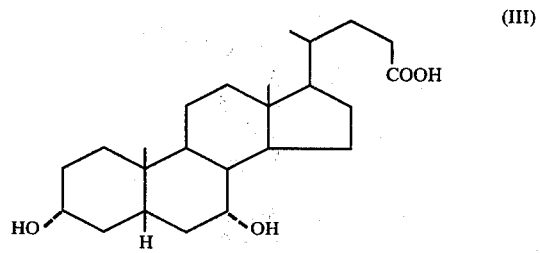

(III)

which comprises reducing a 12-oxocholanic acid tosylhydrazone compound of the following formula

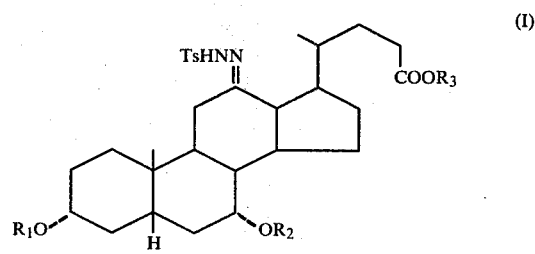

(I)

wherein $R_1$ and $R_2$ are identical or different and each represents an acyl group, Ts represents a tosyl group, and $R_3$ represents an alkyl group, in an organic acid solvent, and subjecting the reduction product to a hydrolyzing treatment.

7 Claims, No Drawings

PROCESS FOR PRODUCTION OF CHENODEOXYCHOLIC ACID

This invention relates to an improved industrial process for producing chenodeoxycholic acid of formula (III) below having a high purity by an easy operation without the need for a complex and disadvantageous purifying procedure.

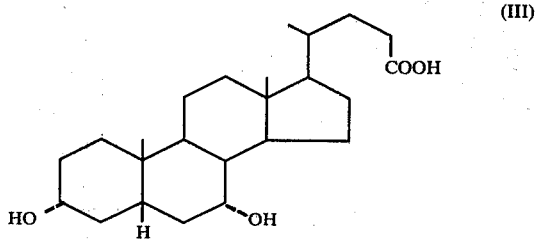

The compound of formula (III) is a known compound having biological activities such as dissolution of gallstones. It is also known as an intermediate for the production of ursodeoxycholic acid useful as a cholagogue.

More specifically, this invention relates to a process for producing chenodeoxycholic acid of formula (III), which comprises reducing a 12-oxocholanic acid tosylhydrazone compound of the formula

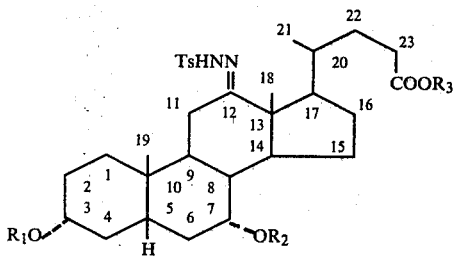

wherein $R_1$ and $R_2$ are identical or different, and each represents an acyl group, Ts represents a tosyl group, and $R_3$ represents an alkyl group, in an organic acid solvent, and subjecting the reduction product to a hydrolyzing treatment.

Many papers have previously been published on the production of chenodeoxycholic acid of formula (III), but the techniques disclosed in these papers cause various troubles when practised on an industrial scale.

One of such techniques is a method which comprises simultaneously reducing and hydrolyzing methyl 3α,7α-diacetoxy-12-ketocholate of the following formula

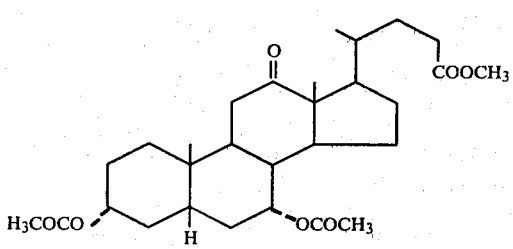

by using hydrazine and an alkali [for example, J. Am. Chem. Soc., 72, 5530 (1950), L. Fieser and S. Rajagopalan; Nature, 169, 621 (1952), I. G. Anderson et al.; Journal of the Japanese Chemical Society, 76, 297 (1955), Kanazawa et al.; Helv. Chim. Acta., 43, 1595 (1960), E. Hauser et al; and Acta. Chem. Scand., 17, 173 (1963), A. F. Hofmann et al.].

The product formed by this reaction contains large amounts of various by-products in addition to chenodeoxycholic acid of formula (III), and is difficult to crystallize. In order to obtain chenodeoxycholic acid of high purity, it is necessary to subject the resulting crude crystals to acetylation and methylation to convert it to methyl 3α,7α-diacetoxycholate of the following formula,

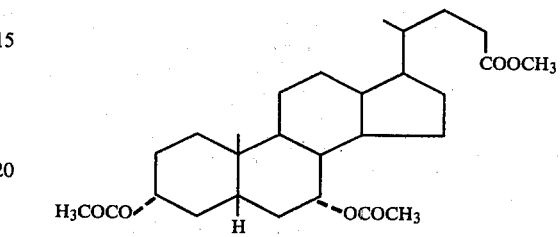

purify it by column chromatography on a filler such as alumina, and hydrolyze the purified product to chenodeoxycholic acid. In addition to this complex operation, the yield of the final product is low. Accordingly, such a process is not suitable for industrial operation.

Sato et al. discloses in J. Org. Chem., 24, 1367 (1959) discloses a process which comprises converting the aforesaid methyl 3α,7α-diacetoxyoxy-12-ketocholate to its 12-thioketal derivative of the following formula

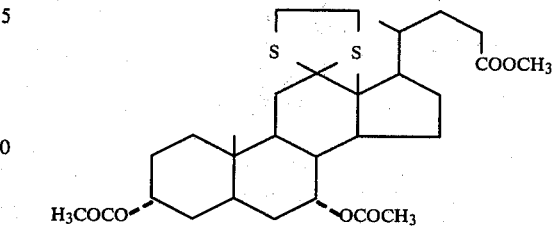

subjecting the 12-thioketal derivative to a desulfurizing reaction, and subjecting the product to a saponification (hydrolysis) treatment to convert it to chenodeoxycholic acid of formula (III). According to this process, too, the inclusion of by-products and the unreacted starting material cannot be avoided, and a purifying procedure is required. Moreover, even by such a purifying procedure, the product is difficult to crystallize. Thus, as in the above-mentioned prior technique, it is necessary to methylate the product, followed by chromatographic purification and hydrolysis. The operation is therefore very complex and the yield is low.

Czechoslovakian Patent No. 186,067 (published on November 15, 1980) discloses a process for producing chenodeoxycholic acid which comprises reducing a tosylhydrazone derivative of 12-oxocholanic acid which embraces the compounds of formula (I) and a compound corresponding to formula (II) in which all of $R_1$, $R_2$ and $R_3$ are hydrogen atoms with sodium borohydride or a diborane derivative, and when $R_1$, $R_2$ and $R_3$ are other than hydrogen atoms, hydrolyzing the reduction product.

This patent states that the compound corresponding to formula (I) in which all of $R_1$, $R_2$ and $R_3$ are hydrogen atoms is preferred to the compound of formula (I) in which $R_1$, $R_2$ and $R_3$ are as defined above. It also discloses the use of a neutral solvent, which is a mixture of tetrahydrofuran and chloroform or ethanol, in the reducing reaction, but is silent on the possibility of using organic acid solvents.

According to a working example of the Czechoslovakian Patent, the product of the reduction in the neutral solvent is obtained as an oil, and it is difficult to obtain it as a highly pure product having a high melting point by an industrially advantageous and easy recrystallizing procedure. The melting point of chenodeoxycholic acid of formula (III) is 172° C. (Gastroenterology, Vol. 73, page 291, 1977; German OLS No. 2,613,346). It is known however that when chenodeoxycholic acid is recrystallized with a solvate-forming solvent, for example a mixture of ethyl acetate and heptane, heptane is bonded in the solvate, and the compound shows a melting point of 119° C. (Lancet, page 111, 1974). The above Czechoslovakian Patent states that on recrystallization from an aqueous ethanol solvent which does not form a solvate, the resulting product has a melting point of 140° to 143° C. In other words, this shows that by an easy and industrially advantageous recrystallizing procedure, a product of high purity having a melting point of about 172° C. cannot be obtained.

The compound of formula (II) used in the synthesis of the compound of formula (I)

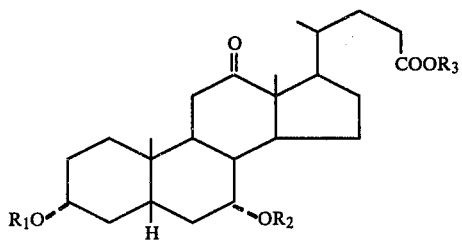

(II)

wherein $R_1$, $R_2$ and $R_3$ are as defined with respect to formula (I), can be industrially produced by esterifying the carboxyl group of 3α,7α,12α-trihydroxy-5β-cholanic acid (cholic acid), of the following formula

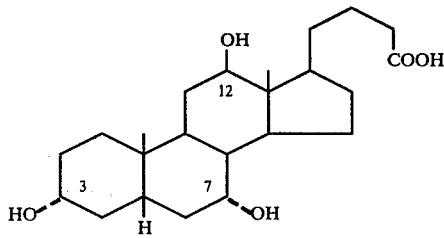

acylating the hydroxyl groups at the 3- and 7-positions to protect these groups, and oxidizing the hydroxyl group at the 12α-position. Accordingly, the compound of formula (II) obtained by the above oxidation reaction is a compound of formula (II) in which $R_1$ and $R_2$ are acyl groups and $R_3$ is an alkyl group. In order to obtain the compound of formula (I) in which all of $R_1$, $R_2$ and $R_3$ are hydrogen atoms and the use of which is recommended in the abovecited Czechoslovakian Patent, it is necessary, for example, to subject the compound obtained by the oxidation reaction further to a hydrolyzing step and then react the product with p-toluenesulfonyl hydrazide. In addition to this disadvantage, the yield of the product in the hydrolysis step is usually about 80 to 85%, and therefore, the product is not an industrially advantageous starting material.

The compound of formula (III) is useful as an agent for dissolving gallstones, and in this use, the presence of impurities formed as by-products during the production of the product of formula (III) may induce undesirable side-effects such as liver diseases. It has been desired therefore to develop a process which can easily produce the compound of formula (III) in high purity with industrial advantage.

The present inventors made investigations in order to develop a new process which can eliminate the defects of the prior techniques, and can easily produce the compound of formula (III) in high purity and good yields on an industrial scale.

These investigations have led to the discovery that by using an industrially advantageous starting compound of formula (I) in which $R_1$, $R_2$ and $R_3$ are other than hydrogen atoms and an organic acid solvent in the reducing reaction, there can be obtained a reduction product in the form of a non-oily substance, and that the hydrolysis product obtained by subjecting the reduction product to a hydrolyzing treatment can be purified by applying an industrially advantageous and easy procedure such as recrystallization to convert it into a highly pure form.

According to the process of this invention, chenodeoxycholic acid of formula (III) having a high purity can be obtained easily without requiring complex operations and treating steps as in the prior art. Chenodeoxycholic acid of formula (III) can be obtained as crystals after the hydrolysis step. If desired, the hydrolysis product may be recrystallized to obtain the compound of formula (III) having a higher purity. Thus, the compound of formula (III) can be produced in a high purity and a high yield without requiring an industrially disadvantageous technique as in the prior art which involves converting the final product to another compound, chromatographing the converted product on a column, and again hydrolyzing the treated product.

The present inventors published in J. Org. Chem. 46, 2786-2788 (issued on June 19, 1981) one example of this new process (a process for producing chenodeoxycholic acid from methyl 3α,7α-diacetoxy-12-ketochlanate via methyl 3α,7α-diacetoxy-12-oxocholate tosylhydrazone).

It is an object of this invention therefore to provide a process which can easily give chenodeoxycholic acid of formula (III) having a high purity from the compound of formula (I) industrially advantageously.

The above and other objects of this invention along with its advantages will become apparent from the following description.

The starting compound of formula (I) can be easily produced in good yields by, for example, contacting a 12-oxocholanic acid compound of formula (II) with p-toluenesulfonyl hydrazide. Upon contact, these reactants are easily condensed to form the compound of formula (I). Heating or cooling is not particularly necessary because the reaction proceeds at room temperature. For example, a reaction temperature of about 0° to about 80° C., preferably about 5° to about 50° C., may be employed. The reaction time can also be selected properly. For example, it is about 3 to about 24 hours, preferably about 10 to about 14 hours.

Preferably, the reaction is carried out in a solvent, for example an organic acid such as acetic acid and propionic acid, a mineral acid such as hydrochloric acid and sulfuric acid, an alcohol such as methanol or ethanol, and a suitable combination of these. The organic acid, especially acetic acid, is preferred.

The mole ratio between the compound of formula (II) and p-toluenesulfonyl hydrazide to be reacted can be suitably selected. For example, about 1 to about 3 moles of p-toluenesulfonyl hydrazide can be used per mole of the compound of formula (II).

After the reaction, the reaction mixture is distilled under reduced or atmospheric pressure to remove the reaction solvent; or extracted with a solvent such as dimethylene chloride, followed by distilling off the extracting solvent from the extract. As a result, the crude compound of formula (I) is obtained. Recrystallization of the crude compound (I) from an alcohol such as methanol easily affords the compound of formula (I) in pure form, and there is no particular need to purify it by a column-chromatographic procedure. Usually, the compound of formula (I) can be obtained in a yield of, for example, about 70 to about 85%.

According to the process of this invention, the starting compound of formula (I) which can, for example, be obtained by the above method is reduced in an organic acid solvent, and the reduction product is subjected to a hydrolyzing treatment to give chenodeoxycholic acid of formula (III) having a high purity. The compound (III) is not formed as an oil.

The process of the invention can be schematically shown below. In the following scheme, Ts, $R_1$, $R_2$ and $R_3$ are as defined hereinabove.

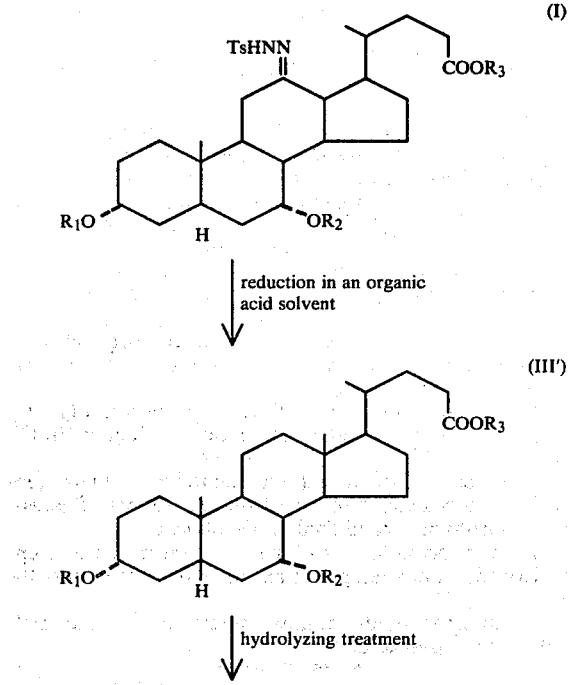

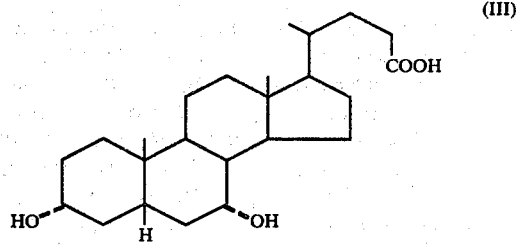

The reducing reaction of the starting compound of formula (I) in the organic acid solvent can be easily carried out by using a metal hydrogen complex such as potassium borohydride and sodium borohydride. The organic acid solvent is, for example, a $C_2$-$C_3$ monocarboxylic acid such as acetic acid or propionic acid. Acetic acid is preferred. The reduction can be performed at room temperature. For example, reaction temperatures of about 20° to about 60° C. can be employed. The amount of the reducing agent can be suitably selected. Preferably, it is about 5 to about 15 moles per mole of the compound of formula (I).

As required, the reaction mixture after the reaction is diluted with a diluent such as water as required, and, if desired, cooled. The crystals separated are collected by filtration to obtain a compound of formula (III') shown above. The compound (III') can be easily purified by recrystallization from dilute methanol, for example. It is not particularly necessary to use a column-chromatographic purifying procedure. Usually, the compound of formula (III') can be obtained in a yield of, for example, about 50 to about 65%.

Examples of the acyl group for $R_1$ and $R_2$ in formulae (I) and (III') are those having 2 and 3 carbon atoms such as an acetyl group and a propionyl group. Examples of the alkyl group for $R_3$ are those having 1 to 3 carbon atoms such as a methyl group, an ethyl group and a propyl group. Compounds of formulae (I) in which $R_1$ and $R_2$ are acetyl groups and $R_3$ is a methyl group are preferred.

The compound of formula (III') so obtained is then subjected to a hydrolyzing treatment to give chenodeoxycholic acid of formula (III) having a high purity in a good yield.

The hydrolysis treatment can be carried out by heating the reducing reduction product in an aqueous solution of an alkali such as sodium hydroxide or potassium hydroxide or an alcoholic solution such as a methanol or ethanol solution of the alkali. The heating temperature is, for example, about 60° to about 110° C.

The amount of the alkali used can be suitably selected. Preferably, it is about 2 to about 20%, especially about 5 to about 10%, in the solution. If desired, the process of the invention can be practised without isolating the compound of formula (III'). In this case, the reduction product mixture is neutralized with an alkali, and the alcoholic solution is added to the neutralized mixture to perform hydrolysis of the reduction product.

Chenodeoxycholic acid (III) so obtained can be further purified easily by a recrystallizing technique using a mixture of ethyl acetate and hexane, or acetonitrile, for example.

Thus, according to the process of this invention, the compound of formula (III) having a high purity can be produced easily in high yields by using a recrystallizing method alone for purification and without the need for complex and disadvantageous operations and treating steps as in the prior art. While the yield of chenodeoxycholic of formula (II) from the 12-oxocholanic acid compound of formula (II) is at most about 10 to about 15% in the conventional methods having the disadvantage of performing complex operations and treating steps, it is about 35 to about 52% in the process of this invention and this increased yield can be achieved without the above disadvantage of the prior art.

The following examples illustrate the present invention more specifically.

EXAMPLE 1

To a solution of 10.1 g (0.02 mole) of methyl 3α,7α-diacetoxy-12-oxo-5β-cholanate in 200 ml of acetic acid was added gradually with stirring 7.5 g (0.04 mole) of p-toluenesulfonyl hydrazide. They were reacted at room temperature for 12 hours. The reaction mixture was diluted with water, and extracted twice with methylene chloride. The methylene chloride layers were combined, and washed with a 5% aqueous solution of sodium bicarbonate and further with water until the product became neutral. The washed product was then dried by a drierite. The solvent was distilled off at 50° C. under reduced pressure, and the resulting oil was treated with a small amount of methanol to crystallize it. Recrystallization from methanol gave 9.7 g (yield 72%) of methyl 3α,7α-diacetoxy-12-oxo-5β-cholanate tosylhydrazone as needlelike crystals.

Melting point: 146° C. to 147° C.

IR (KBr): 5.80 (C=O), 3.15, 6.15, 6.30, 7.52, 8.65 (s), and 12.31 μm (tosylhydrazone).

NMR δ (CDCH$_3$): 0.81 (3H, s, C-18CH$_3$), 0.96 (3H, s, C-19CH$_3$), 2.00 and 2.01 (both 3H, s, OCOCH$_3$), 2.42 (3H, s, ArCH$_3$), 3.65 (3H, s, OCH$_3$), 4.51 (1H, broad m, C-3CHOCOCH$_3$), 4.91 (1H, m, C-7CHOCOCH$_3$), and 7.32 and 7.76 (both 2H, d, J=9 Hz, ArH).

Elemental analysis for C$_{36}$H$_{52}$N$_2$O$_8$S:

|  | C | H |
| --- | --- | --- |
| Calculated: | 64.26% | 7.79% |
| Found: | 63.91% | 7.88% |

EXAMPLE 2

In a flask, 4.04 g (0.006 mole) of methyl 3α,7α-diacetoxy-12-oxo-5β-cholanate tosylhydrazone obtained in Example 1 was dissolved in 80 ml of acetic acid, and with stirring, 2.27 g (0.06 mole) of sodium borohydride was added so that the reaction temperature did not exceed 60° C. (this required a period of about 1 hour). The mixture was stirred further at room temperature for 3 hours. The flask was dipped in an ice bath, and ice cubes were gradually added with stirring. The precipitate formed was collected by filtration, washed with water, and recrystallized from aqueous methanol to give 1.78 g (yield 60%) of methyl 3,7-diacetyl-chenodeoxycholate as needlelike crystals.

Melting point: 133° C. to 133.5° C.

IR (CHCl$_3$): 5.80 (C=O), 9.38, 10.33 μm(C=O).

NMR δ (CDCl$_3$): 0.64 (3H, s, C-18CH$_3$), 0.92 (3H, s, C-19CH$_3$), 2.00 and 2.02 (both 3H, s, OCOCH$_3$), 3.63 (3H, s, O-MeCH$_3$), 4.56 (1H, broad m, C-3CHOCOCH$_3$), 4.88 (1H, m, C-7CHOCOCH$_3$).

Elemental analysis for C$_{29}$H$_{46}$O$_6$:

|  | C | H |
| --- | --- | --- |
| Calculated: | 70.98% | 9.45% |
| Found: | 71.30% | 9.24% |

Two grams of the resulting methyl 3,7-diacetyl-chenodeoxycholate was reduced under heat in 40 ml of a 10% methanol solution of potassium hydroxide for 12 hours, and then, the solvent was distilled off. The residue was dissolved in water, and with cooling by ice, acidified with 3 N hydrochloric acid. The precipitate formed was washed with water, dried at 100° C., and recrystallized from ethyl acetate/hexane to give 1.60 g (yield 96%) of chenodeoxycholic acid as needlelike crystals.

Melting point: 119.5° C. to 121° C. (ethyl acetate/hexane), 167.5° C. to 172.5° C. (acetonitrile).

IR (KBr): 5.92 (C=O), 9.34, and 10.25 μm (C=O).

Thin-layer chromatography (chloroform/ethyl acetate/acetic acid=45/45/10): Rf=0.80 (single spot).

What we claim is:

1. A process for producing chenodeoxycholic acid of the following formula

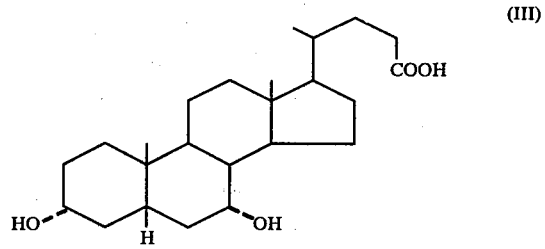

which comprises reducing a 12-oxocholanic acid tosylhydrazone compound of the following formula

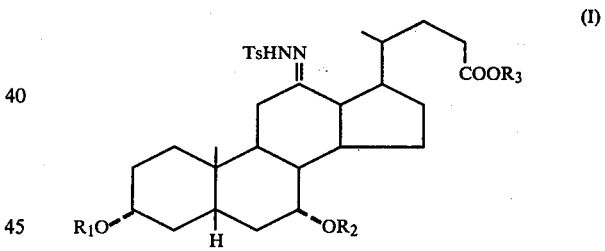

wherein R$_1$ and R$_2$ are identical or different and each represents an acyl group, Ts represents a tosyl group, and R$_3$ represents an alkyl group, with a metal hydrogen complex in an organic acid solvent, and subjecting the reduction product to a hydrolyzing treatment in an aqueous or alcoholic solution of an alkali.

2. The process of claim 1 wherein the reduction is carried out at a temperature of about 20° C. to about 60° C.

3. The process of claim 1 wherein the organic acid solvent is at least one monocarboxylic acid having 2 or 3 carbon atoms.

4. The process of claim 1 wherein the hydrolyzing treatment is carried out at a temperature of about 60° C. to about 110° C.

5. The process of claim 1 wherein the metal hydrogen complex is selected from the group consisting of potassium borohydride and sodium borohydride.

6. The process of claim 1 wherein the reduction step is carried out at a temperature of about 20° to about 60° C.

7. The process of claim 3 wherein the organic acid solvent is acetic acid.

* * * * *